United States Patent [19]
Callahan et al.

[11] Patent Number: 4,852,566
[45] Date of Patent: Aug. 1, 1989

[54] DEVICE FOR IMPLANTATION OF INTRAOCULAR LENS

[76] Inventors: Wayne B. Callahan, 5119 Woodland Hills Dr., Brentwood, Tenn. 37207; James E. Burnes, 610 W. Due West Ave., Madison, Tenn. 37115

[21] Appl. No.: 214,808

[22] Filed: Jul. 1, 1988

Related U.S. Application Data

[63] Continuation of Ser. No. 928,500, Nov. 7, 1986, abandoned.

[51] Int. Cl.[4] ............................ A61F 1/16; A61F 9/00
[52] U.S. Cl. ................................................. 128/303 R
[58] Field of Search ........................ 128/303 R; 623/6

[56] References Cited

U.S. PATENT DOCUMENTS

| 4,053,953 | 10/1977 | Flom et al. | 128/303 R X |
| 4,136,406 | 1/1979 | Norris | 623/6 |
| 4,190,049 | 2/1980 | Hager et al. | 128/303 |
| 4,198,980 | 4/1980 | Clark | 128/303 |
| 4,325,375 | 4/1982 | Nevyas | 128/305 |
| 4,326,306 | 4/1982 | Poler | 3/13 |
| 4,349,027 | 9/1982 | DiFrancesco | 128/303 |
| 4,423,809 | 1/1984 | Mazzocco | 206/5.1 |
| 4,527,294 | 7/1985 | Heslin | 128/303 R X |
| 4,530,117 | 7/1985 | Kelman | 623/6 |
| 4,619,256 | 10/1986 | Horn | 128/303 |
| 4,634,423 | 1/1987 | Bailey | 604/51 |

FOREIGN PATENT DOCUMENTS 2153688  8/1985  United Kingdom ............ 128/303 R

Primary Examiner—Michael H. Thaler
Attorney, Agent, or Firm—James A. Arno; Gregg C. Brown

[57] ABSTRACT

A device for controlling the release of retracted haptics on an intraocular lens is described. By controlling the retraction of the haptics, it is possible to obtain a more precise placement of the lens in the eye. The lens is attached to the device by means of sutures, which allows the lens to be safely and conveniently positioned in the eye.

8 Claims, 3 Drawing Sheets

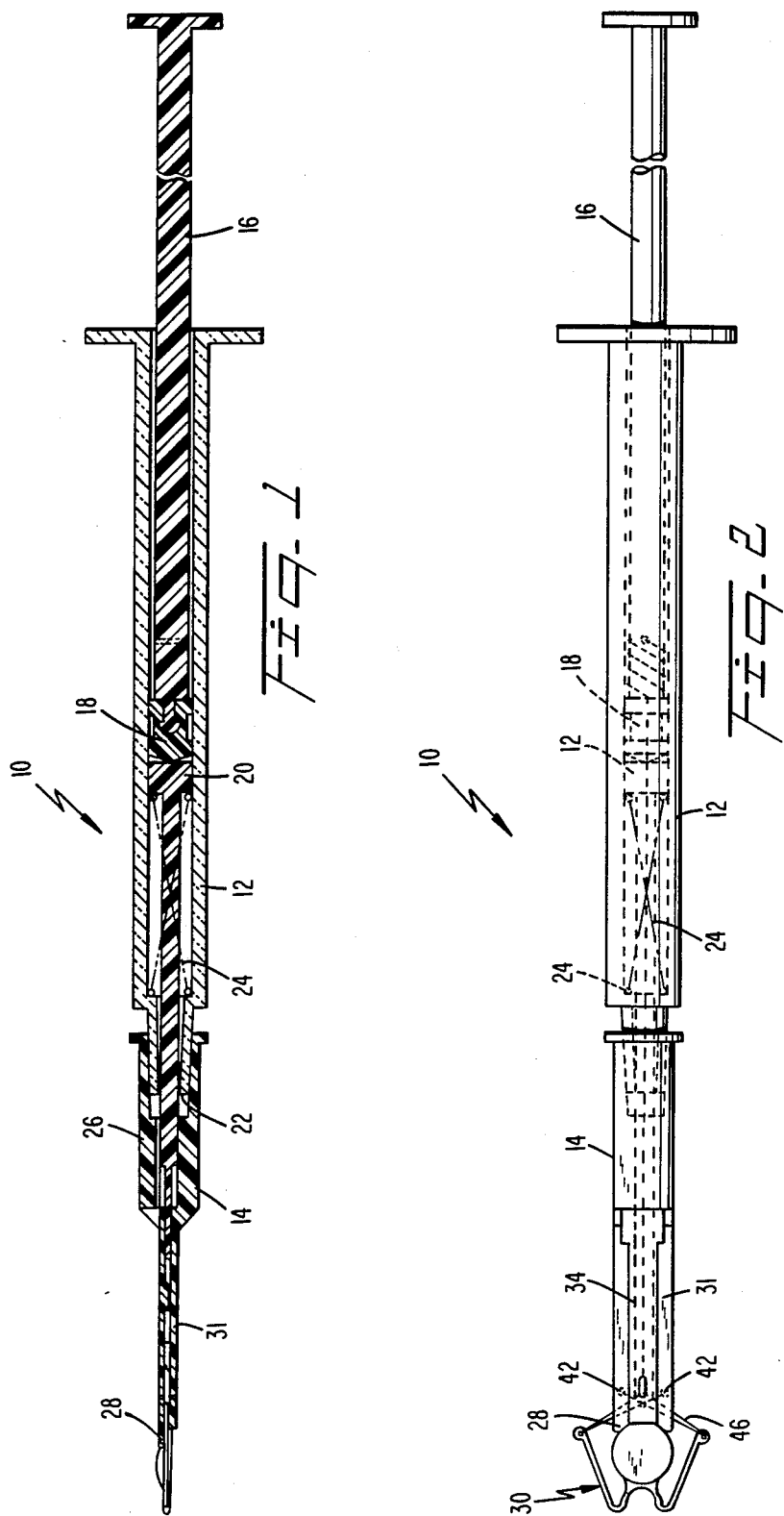

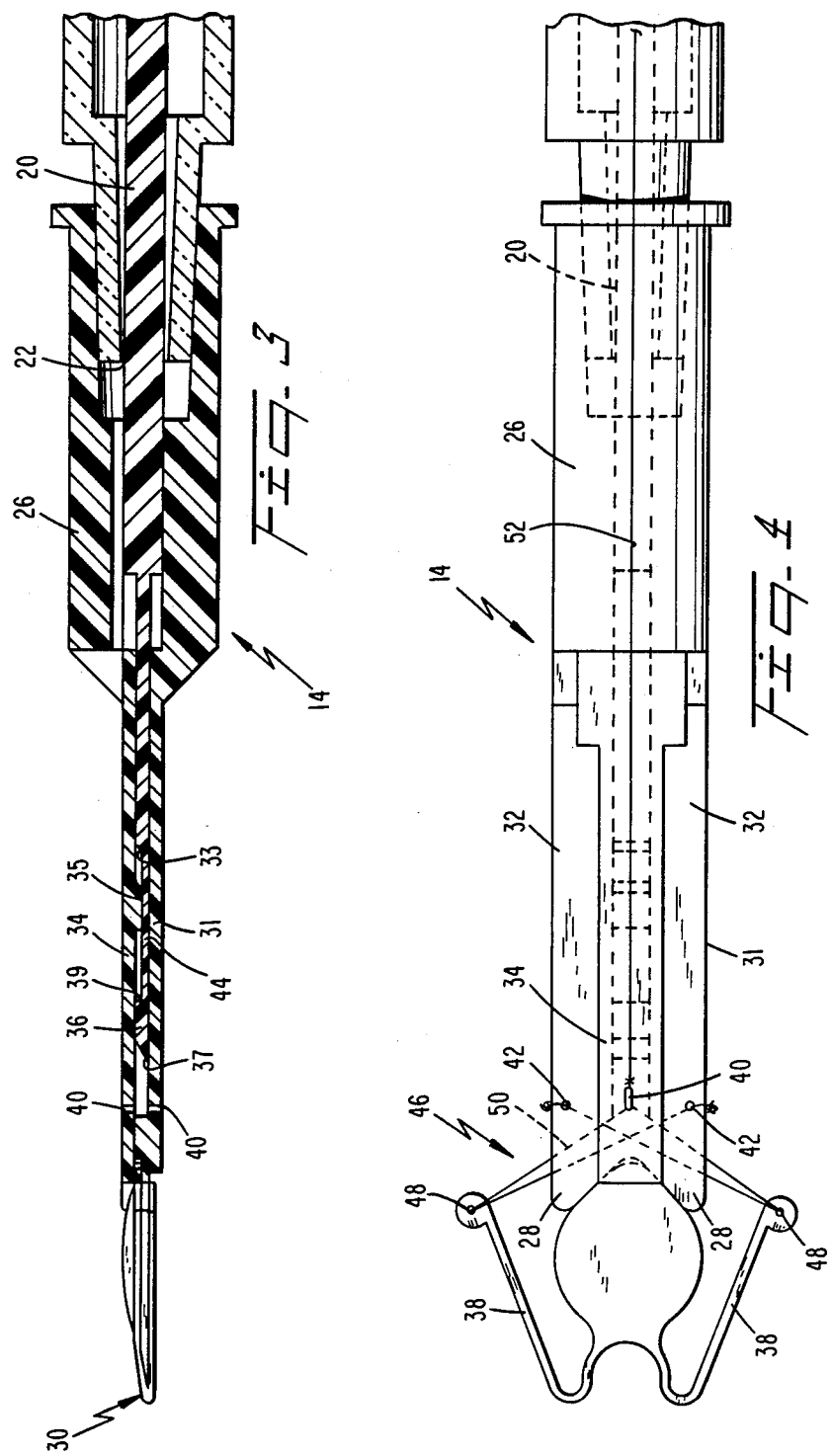

DEVICE FOR IMPLANTATION OF INTRAOCULAR LENS

This is a continuation of application Ser. No. 928,500, filed 11/7/86, now abandoned.

BACKGROUND OF THE INVENTION

1. Field of the Invention

The present invention relates to the field of intraocular lenses. More particularly, this invention relates to a device which is useful in the surgical implantation of artificial lenses to replace the natural crystalline lens of the human eye.

2. Discussion of Related Art

The field of intraocular lenses and associated devices has grown very rapidly over the last decade. Numerous intraocular lens designs have been proposed during this period, during which the art has progressed from relatively crude designs wherein the lens was sutured or otherwise physically attached to the iris to the prsent state of the art wherein the lens is supported in the anterior or posterior chambers independently of any attachment to the iris. Another respect in which the art has progressed is the size of the incision required to insert the lens. Because of improved surgical techniques and associated improvements in lens designs, the incisions typically utilized today are much smaller than those used just a few years ago. There are, of course, other respects in which the art has advanced. Despite such advancements, the surgical replacement of the natural crystalline lens of the eye with an artificial lens still remains a very delicate surgical procedure. Special surgical skills and expertise are required for this procedure. For example, the proper placement of a lens in the eye upon implantation requires an intimate familiarity with the internal anatomy of the eye and the forces which will affect proper placement of lens both during and after implantation. It can be very difficult to reposition a lens once it is placed in the eye. It is also generally difficult to place the lens properly in the eye on the first attempt. In light of these difficulties, there is a great need for a device which will allow the lens to be inserted and properly positioned upon initial insertion into the eye. The present invention is directed to a device which satisfies this need.

Reference is made to the following patents for further teachings regarding the state of the intraocular lens art, particularly the portion of that art relating to devices for use in implanting intraocular lenses:

U.S. Pat. No. 4,325,375 (Nevyas)
U.S. Pat. No. 4,349,027 (DiFrancesco)
U.S. Pat. No. 4,136,406 (Norris)
U.S. Pat. No. 4,190,049 (Hager, et al.)
U.S. Pat. No. 4,198,980 (Clark)
U.S. Pat. No. 4,423,809 (Mazzocco)
U.S. Pat. No. 4,530,117 (Kelman)

None of the devices described in these patents satisfy the above-cited need for a device which will facilitate proper insertion of intraocular lenses.

SUMMARY OF THE INVENTION

A principal object of the present invention is the provision of a device which will enable the ophthalmic surgeon to control the positioning of an intraocular lens in the eye in a manner such that proper placement of the lens is facilitated.

Another object of the present invention is the provision of an intraocular lens insertion device which is convenient and noncumbersome.

The foregoing objectives and other general objectives of the present invention are achieved by the provision of a device which comprises a means for retracting and releasing the haptics of an intraocular lens in a manner such that the device and a lens attached thereto with its haptics retracted can be easily placed through the incision, and that the lens can then be properly and easily positioned by controlling the retraction of the haptics to allow for proper positioning of the lens prior to releasing the lens from the device and withdrawing the device from the eye.

BRIEF DESCRIPTION OF THE DRAWINGS

FIG. 1 is a longitudinal, cross-sectional view of an intraocular lens insertion device according to the present invention;

FIG. 2 is a top view of the device illustrated in FIG. 1;

FIG. 3 is a partial, enlarged, cross-sectional view of the forward end of the device illustrated in FIG. 1;

FIG. 4 is a top view of the portion of the device illustrated in FIG. 3;

DETAILED DESCRIPTION OF PREFERRED EMBODIMENT

Figure 5:
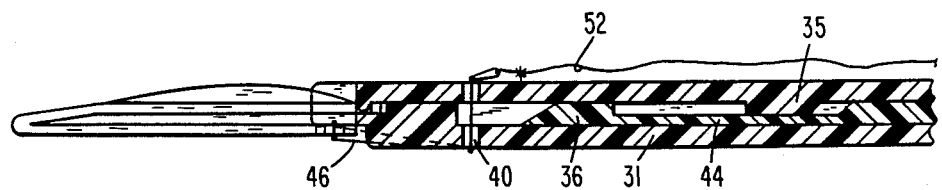
FIG. 5 is an enlarged, cross-sectional view of the forward tip of the device.

Referring first to FIGS. 1 and 2, it can be seen that the device of the present invention 10 comprises a syringe portion 12 and an instrument portion 14. The syringe portion 12 is a standard hypodermic injection syringe which includes a plunger 16 and a piston 18 attached to the forward end of the plunger. The type of syringe utilized in the present invention is not critical. Disposable, plastic syringes of the type utilized for insulin injections are preferred, due to factors such as cost and availability.

A release plunger 20 is disposed in the forward end of the syringe 12, and extends through an opening 22 at the tip of the syringe into the instrument portion 14, as best shown in FIGS. 1 and 3. A coil spring 24, shown by means of diagonal lines in FIG. 1, is disposed in the forward end of the syringe 12. The spring 24 biases the release plunger 20 toward the rear of the syringe 12.

The instrument portion 14 is attached to the forward end of syringe 12. The instrument portion comprises a cylindrical portion 26 adapted for attachment to the forward end of the syringe 12, a lens holding portion 28 adapted to hold or support the optical portion of an intraocular lens 30, a body portion 31 extending between the cylindrical portion 26 and the lens holding portion 28, and a retaining clip 34 disposed on the upper surface of body portion 31, seated in a groove formed by the sides 32 of the body support portion 31. The retaining clip 34 includes a downwardly projecting protuberance 35. The forward end of the retaining clip 34 and the body portion 31 are penetrated by a common opening or hole 40 near the forward ends thereof. The sides 32 of longitudial support portion 31 are each provided with holes 42.

The forward end 36 of release plunger 20 has a tapered edge 37. The portion of the release plunger located just rearwardly from forward portion 36 is of reduced thickness; this area of reduced thickness is identified by means of reference numeral 44 in FIGS. 3 and 5.

Figure 6:
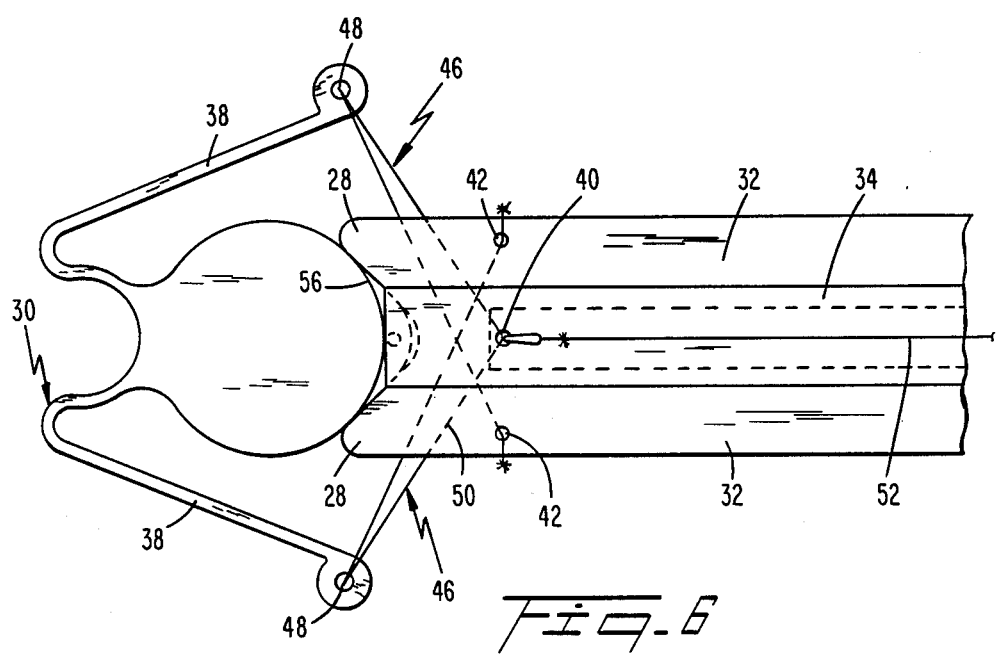
FIG. 6 is a top view of the portion of the device illustrated in FIG. 5, showing in detail the harness arrangement utilized to control the retraction of the haptics on an intraocular lens.

As illustrated in FIGS. 2, 4, 5 and 6, a harness 46 is utilized to retract the haptics 38 of the lens 30 and secure the lens to the device at its forward tip 28. The harness 46 is threaded thru openings 48 in the free ends of the haptics 38. Free ends of the harness are secured to the holes 42 in arm portions 32 of body portion 31. As illustrated in FIGS. 4 and 6, the free ends of the harness are secured to a hole 42 on a side of the body portion opposite from the free end of the haptic which is being secured. A generally V-shaped bridle portion 50 of the harness 46 has its midpoint located over the opening 40 in the tongue portion. As shown in FIGS. 2, 5 and 6, the bridle 46 travels through opening 40 and has a separate segment 52 which extends between opening 40 and the piston 18 of syringe 12 where it is secured. The harness will typically be made from sutures, such as those commonly used in surgery. In the embodiment of the invention illustrated in the drawings, a USP size 7-0 silk suture is utilized for segment 52 of the bridle and a USP size 9-0 silk suture is utilized for the portion of the bridle which is directly attached to the lens. In choosing an appropriate size and type of suture, it should be kept in mind that the suture must be strong enough to restrain the haptics of the lens without breaking, but yet light enough to release easily from the haptics when the bridle is severed by edge 37 of release plunger 20. The operation of the above-described is further described below.

The projection 35 on the lower side of retainer clip 34 interacts with the area of reduced thickness 44 in the forward end of the release plunger to provide the device with the ability to both retract and release the haptics 38 of the lens 30. The extent to which the haptics can be retracted or released is directly related to the length of the area of reduced thickness 44. The haptics cannot be retracted beyond the point at which the rear face 39 of the forward portion 36 of the release plunger 20 is in contact with projection 35. The coil spring 24 located in the syringe will keep the released plunger in this position. As the surgeon depresses the syringe plunger 16, the release plunger 20 is moved forward and tension on harness 46 is relaxed, thereby releasing the haptics. As the surgeon manipulates the lens in an attempt to achieve proper placement in the eye, he or she may adjust the tension on the harness by gradually depressing or releasing pressure on the syringe plunger 16. By depressing the syringe plunger 16 to a point at which projection 35 is in contact with a point 33 on the release plunger of greater thickness, the surgeon can virtually totally release the haptics without releasing the lens from the device. When the syringe plunger 16 is depressed beyond this point two things happen. The sharp edge 37 severs the harness, and the retaining clip 34 is raised upwardly as the projection 35 is contacted by the thicker portion of the release plunger, beginning at point 33. The severing of the harness results in total release of the haptics. The raising of the retaining clip 34 results in release of the lens from its generally hemispherical seat 56 at the tip of body portion 31; this release occurs when the forward end of the retaining clip 34 is elevated to a point at which it leaves contact with the lens. At this point, the implantation is complete, and the instrument is removed from the eye.

What is claimed is:

1. A device for implanting intraocular lenses in the eye, comprising syringe means, including a plunger and a piston attached to a forward end of the plunger; intraocular lens holding means secured to a forward end of the syringe means; a harness having a first end attached to said piston and a second end adapted for connection to a haptic of the intraocular lens to transmit tension to the haptic as a function of the location of the piston in the syringe means; and severing means connected for movement with the piston for severing the harness; whereby depression of the plunger causing movement of the piston can be used to control tension applied to the haptic through the harness to decrease retraction of the haptic and release of the plunger can be used to increase retraction of the haptic allowing for control and adjustment of the haptic, and depression of the plunger causing movement of the piston and thereby the severing means through a predetermined distance results in severing of the harness and release of the haptic from the forward end of the syringe means.

2. The device of claim 1, further including a release plunger interposed between the piston and severing means in the syringe means and spring means for biasing the release plunger and thereby the piston and plunger in the direction of increased retraction of the haptic.

3. The device of claim 2, wherein said release plunger has a sharp forward end being said severing means.

4. The device of claim 3, further including control means mounted on the syringe means for controlling the extent of forward travel of the severing means through said predetermined distance.

5. The device of claim 4, wherein said control means includes a clip extending along a forward end body portion of the syringe means, said clip including a protuberance interfitting within a portion of the release plunger of reduced thickness having opposite front and rear end shoulders, the front shoulder limiting retraction of the release plunger in the rearward direction of the syringe means by contact of the protuberance with the front shoulder.

6. The device of claim 5, wherein said clip is mounted in a groove formed in the forward end body portion, a front end of said clip establishing a seat with the forward end of the body portion in contact with the lens, whereby movement of the release plunger and severing means through the predetermined distance causes the rear shoulder to contact the protuberance to lift the clip away from the body portion and enable the lens to release from the seat as the severing means severs the harness.

7. The device of claim 6, wherein said syringe means includes a syringe portion and an instrument portion detachably mounted to a forward end of the syringe portion, said instrument portion defining the forward end body portion.

8. The device of claim 7, wherein said spring means is interposed between a rear end of the release plunger and a forward end of the syringe portion.

* * * * *